(12) United States Patent
Srinivasan et al.

(10) Patent No.: US 8,062,515 B2
(45) Date of Patent: Nov. 22, 2011

(54) PARKING A SAMPLE STREAM AND SUPPRESSING THE SAMPLE

(75) Inventors: Kannan Srinivasan, Tracy, CA (US); Rong Lin, Sunnyvale, CA (US)

(73) Assignee: Dionex Corporation, Sunnyvale, CA (US)

( * ) Notice: Subject to any disclaimer, the term of this patent is extended or adjusted under 35 U.S.C. 154(b) by 770 days.

(21) Appl. No.: 12/140,522

(22) Filed: Jun. 17, 2008

(65) Prior Publication Data

US 2008/0245668 A1    Oct. 9, 2008

Related U.S. Application Data

(62) Division of application No. 10/934,792, filed on Sep. 2, 2004, now Pat. No. 7,399,415.

(51) Int. Cl.
*B01D 15/08* (2006.01)
(52) U.S. Cl. ............ 210/198.2; 210/635; 210/638; 210/656; 210/659
(58) Field of Classification Search .......... 210/635, 210/638, 644, 656, 659, 748, 198.2, 243; 204/520, 630; 436/100, 150, 161, 175
See application file for complete search history.

(56) References Cited

U.S. PATENT DOCUMENTS

| | | |
|---|---|---|
| 4,962,042 A | 10/1990 | Morabito et al. |
| 4,999,098 A | 3/1991 | Pohl et al. |
| 5,569,365 A | 10/1996 | Rabin et al. |
| 5,597,481 A | 1/1997 | Stillian et al. |
| 6,808,608 B2 | 10/2004 | Srinivasan et al. |

FOREIGN PATENT DOCUMENTS

| | | |
|---|---|---|
| WO | WO 94/02227 A1 | 2/1994 |
| WO | WO 97/22876 A1 | 6/1997 |

OTHER PUBLICATIONS

De Borba, B., et al., "Online dialysis as a sample preparation technique for ion chromatography," *J. Chromatogr.* 919(1):59-65 (Jun. 2001).
Haddad, P., et al., "Developments in suppressor technology for inorganic ion analysis by ion chromatography using conductivity detection," *J. Chromatogr. A* 1000(1-2):725-742 (Jun. 2003).
Montgomery, R., et al., "Online sample preparation techniques for ion chromatography," *J. Chromatogr. A* 804(1-2):55-62 (Apr. 1998).

*Primary Examiner* — Ernest G Therkorn
(74) *Attorney, Agent, or Firm* — Morgan, Lewis & Bockius LLP; David J. Brezner

(57) ABSTRACT

Pretreatment method and apparatus to remove matrix ions from a liquid sample, prior to separation of the sample analytes (e.g. by chromatography), by flowing the liquid sample into a sample compartment and stopping the flow. The sample compartment has a wall comprising an ion exchange membrane having exchangeable ions of the same charge as the matrix ions to be removed. A regenerant liquid stream flows through a regenerant flow compartment on the other side of the membrane from said parked liquid sample. Matrix ions in the parked liquid sample are transported across the membrane into the regenerant flow compartment. Suppression may be performed electrolytically and/or chemically. A concentrator column may also be used.

4 Claims, 13 Drawing Sheets

PARKING A SAMPLE STREAM AND SUPPRESSING THE SAMPLE

CROSS REFERENCE TO RELATED APPLICATION

This application is a divisional application of U.S. application Ser. No. 10/934,792 filed on Sep. 2, 2004, now U.S. Pat. No. 7,399,415.

BACKGROUND OF THE INVENTION

In suppressed ion chromatography a suppressor device is used to remove either anions or cations from the eluent thereby, reducing the eluent to a weakly dissociated form. The analyte ion is typically converted to a conductive form thereby allowing detection of the analyte against a low background. Different types of suppressors have evolved over the years. The early suppressor devices used chemical means for accomplishing suppression. Typically an acid or base regenerant supplied the regenerant ions. Other types of suppressors use electrolytically generated ions to achieve suppression. Representative suppressor devices included packed bed suppressors, fiber suppressors, flat membrane and based suppressors. The above devices are typically operated with the regenerant flowing countercurrent to the eluent stream. In one form of electrolytic suppression the suppressed effluent is recycled from the detector for use as the source of water required for the electrolytic water splitting reactions. This mode of operation was called the recycle mode. In another mode called the external water mode of operation, the suppressor regenerant channels are supplied with water from an external source that is electrolytically split thereby forming the regenerant required for the suppression reaction. In this mode the external reservoir is replenished with water. Typically this mode was recommended for solvent containing eluents or when there was a need for improving the detection limits since this mode lowered the background noise.

Different forms of flat membrane suppressors is described in U.S. Pat. No. 4,999,098. In one, the suppressor includes at least one regenerant compartment and one chromatographic effluent compartment separated by an ion exchange membrane sheet. The sheet allows transmembrane passage of ions of the same charge as its exchangeable ions. Flow from the effluent compartment is directed to a detector, such as an electrical conductivity detector, for detecting the resolved ionic species. A sandwich suppressor is also disclosed including a second membrane sheet opposite to the first membrane sheet and defining a second regenerant compartment. Spaced electrodes are disclosed in communication with both regenerant chambers along the length of the suppressor. By applying an electrical potential across the electrodes, there is an increase in the suppression capacity of the device. The patent discloses a regenerant solution (acid or base) flowing in the regenerant flow channels and supplied from a regenerant delivery source. The patent also discloses the possibility of using water to replace the regenerant solution in the electrodialytic mode.

One potential problem with ion chromatography or other analytical methods such as high performance liquid chromatography (HPLC) is when the sample liquid contains a matrix of one or more compounds of high ionic strength. For chromatography, the sample peaks may be obscured by large interfering peaks of a matrix ion of the matrix compounds. Also, the chromatographic results can be significant also because the matrix ion is of such high concentration that it becomes the major eluting ion, temporarily overriding the eluent.

A membrane suppressor device used in ion chromatography (e.g., of one of the general type set forth in U.S. Pat. No. 4,999,098) has been used as a pretreatment device on-line with subsequent chromatographic separation using ion chromatography. Pretreatment reduces the concentration of the matrix ions of acid or base matrices. This technique is useful for the analysis of anions and cations only when the sample matrix is basic or acidic, respectively. This is because the suppressor device is also an ion exchange device, cation exchange for anion analysis and anion exchange for cation analysis. For example, neutralization of a basic matrix for analyzing anions requires the removal of the cationic co-ion to the hydroxide ion and replacing with a hydronium ion to form water for the neutralization reaction. The removal and replacement occur at ion exchange sites in the pretreatment device.

For some samples, continuous membrane based suppressor pretreatment device operated in the chemical mode may have the required capacity to treat the matrix ion. However, it may produce an interfering blank (e.g., sulfate for anion analysis with sulfuric acid as the regenerant). This is due to potential leakage of the acid regenerant used to supply the continuous source of hydronium ion for the neutralization reaction across the membrane.

A commercial neutralizer product sold by Dionex Corporation under the trademark ASRN was used as a pretreatment device for analyzing anions in a base stream. The published maximum dynamic suppression capacity of the ASRN suppressor is about 200 ueqv/min or about 200 mM at a flow rate of 1 ml/min. While this capacity is acceptable for most samples, it is difficult to suppress high concentrations of acid or base sample using one pass of the sample particularly at larger sample volumes. The larger sample volume requirement stems from the need to be able to detect trace ions with high sensitivity.

U.S. Pat. No. 5,597,481 discloses one approach to suppressing high concentrations and large sample volumes of acid or base matrices by passing the sample multiple times through the suppressor eluent channel thereby utilizing the regenerated capacity of the suppressor device. Currents as high as 500 mA was used to maximize the suppressable concentration. As disclosed, the device is in the form of an electrochemical membrane device in which sample flows through a sample flow channel of the device separated from a regenerant flow channel by an ion exchange membrane preferentially permeable to the same charge as the matrix ions and including exchangeable ions of that one charge. The pretreatment device includes electrodes in electrical communication with the sample flow channel and regenerant flow channel. The ionic species in the pretreatment sample device are directed to an analytical system comprising means for separating the ionic species and detector means for detecting the separated ionic species. One form of the pretreatment device includes two ion exchange membranes defining the sample flow channel. Two regenerant channels are on either side of the sample flow channel and are separated by the ion exchange membranes. The electrodes are in these outside flow regenerant channels. In another embodiment, the disclosed apparatus includes ionic species concentration column disposed downstream of, and in communication with, the pretreatment means for collecting and concentrating the ionic species to be detected. After concentration, the ionic species are eluted from the concentration means and directed to the analytical system. In a further disclosed embodiment, for use with a sample for which the pretreatment device has insufficient capacity, a conduit was disclosed for recycling the liquid sample stream to the sample flow channel as many times as desired to accomplish pretreatment prior to flow to the analytical system.

SUMMARY OF THE INVENTION

One embodiment of the invention comprises a method comprising (a) parking liquid sample including said ionic species and at least one matrix compound including matrix ions of opposite charge to said ionic species, said parking being performed by flowing said liquid sample into a sample compartment and stopping said flow, said sample compartment having a first wall comprising at least one ion exchange membrane capable of transporting ions of one charge, positive or negative, and having exchangeable ions of the same charge as said matrix ions, said parked liquid sample being on one side of said one membrane, (b) flowing a regenerant liquid stream through a regenerant flow compartment on the other side of said one membrane from said parked liquid sample, (c) transporting at least some of said matrix ions in said parked liquid sample across said one membrane into said regenerant flow compartment to be carried away in said regenerant solution, (d) after step (c), removing said liquid sample from said sample compartment, and (e) separating said ionic species in said removed liquid sample.

Another embodiment of the invention comprises an apparatus comprising (a) a pretreatment device for pretreating an aqueous sample stream comprising a plurality of ionic species to be detected and at least one matrix compound for removing at least part of the matrix ions of such matrix compound, said matrix ions being of opposite charge to said ionic species, and replacing said matrix ions with hydroxide or hydronium ions, said pretreatment device including (1) a sample compartment having an inlet and an outlet, (2) a regenerant compartment having an inlet and an outlet, (3) at least one ion exchange membrane partitioning said sample compartment and said regenerant compartment, said one ion exchange membrane being preferentially permeable to ions of one charge only, positive or negative, of the same charge as said matrix ions, and including exchangeable ions of said one charge, (b) a separator comprising chromatographic medium for separating the ionic species in said pretreated sample stream in fluid communication with said sample compartment outlet, and (c) a detector for detecting said separated ionic species in fluid communication with said separator, (d) a pump for transporting aqueous sample through said pretreatment device, and (e) a timing controller for turning off said pump or switching a valve in communication with said pretreatment device for a predetermined duration related to the desired extent of replacement of said matrix ions in said aqueous sample.

DETAILED DESCRIPTION OF THE PREFERRED EMBODIMENTS

Figure 1:
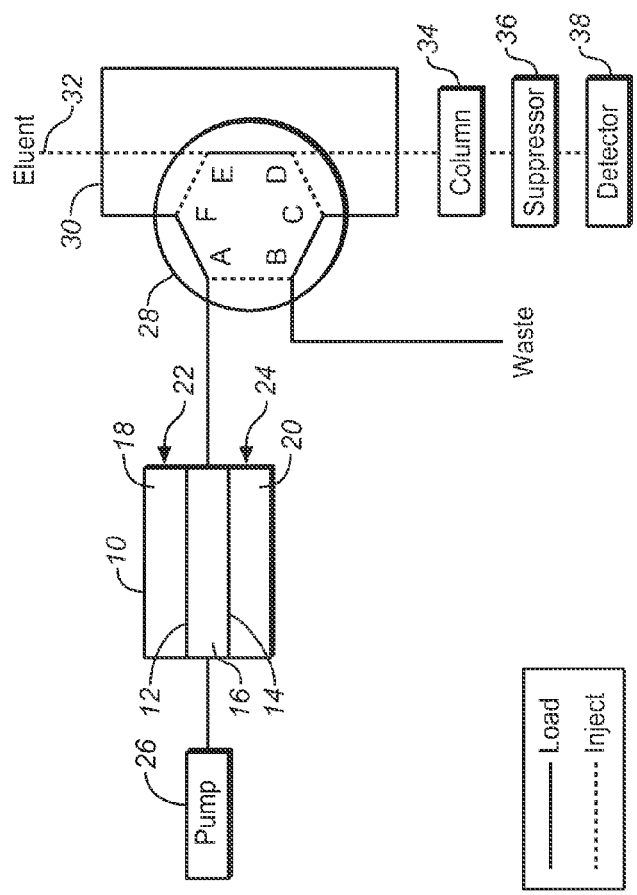
FIGS. 1-4A-E are schematic flow diagrams of apparatus for performing chromatography using the electrochemical pretreatment system of the present invention.

The system of the present invention is useful for determining a number of ionic species in a sample containing a matrix compound so long as the species to be determined are solely anions or solely cations.

When the term "ionic species" is used herein, it includes species in ionic form and components of molecules which are ionizable under the conditions of the present system.

The present invention relates to the pretreatment of a parked sample using a suppressor-like pretreatment device including a permselective membrane. The terms "park" and "parking" and variations of these terms refer to flowing liquid sample into the pretreatment device and then stopping the flow for a predetermined duration during which suppression-like reactions are performed to remove matrix ions from the sample stream.

As used herein, the term "matrix compound" means a compound such as an acid or base capable of being suppressed or neutralized by removal of the matrix ion portion of the matrix compound of opposite charge to the anionic or cationic analytes of interest by removal through the ion exchange membrane of the pretreatment device. The matrix ion is replaced by hydroxide or hydronium ion forming a substantially unionized compound, such as water. The analyte ions are converted to acidic or basic forms.

For anion analysis, the matrix compound may be a base (typically NaOH or other alkali metal hydroxides). Other possible matrix compounds include sodium carbonate, sodium borate, ammonium hydroxide, amines or tetra-alkyl ammonium hydroxides such as tetramethyl or tetrabutyl ammonium hydroxide. For cation analysis, the matrix compound may be an acid, typically a common mineral or organic acid (e.g., sulfuric acid, phosphoric acid or methane sulfonic acid).

The pretreatment technique is used when the matrix ion of the matrix compound is present at a sufficient concentration relative to the ionic species to be detected to interfere with separation, as by chromatography, or subsequent detection. A typical minimum concentration to warrant use of the system is when the matrix ion is present at least 2-10 times the molar ionic concentration of the chromatographic eluent.

An important aspect of the present invention is parked suppression in which the sample solution is stationary or non-flowing in a pretreatment device sample compartment while the suppressor is regenerated, preferably continuously, either by electrolytic means or chemical means. The sample stream is stationary during the suppression process.

Suppressor devices of the prior art in which a regenerant solution flows on the opposite side of a permselective membrane from a flowing liquid sample stream may be used that are continuously or intermittently regenerated for parked pretreatment according to the invention. Representative suppressors which can be used for the pretreatment devices include those disclosed in U.S. Pat. Nos. 4,999,098, 5,248,426, 5,569, 365, 6,077,434, 6,328,885 and 6,495,371.

More specifically, the liquid sample including ionic species of one charge, positive or negative, in a liquid sample including at least one matrix compound having matrix ions of opposite charge to the ionic species are parked in a sample compartment of the pretreatment device. The compartment has a wall comprising at least one permselective ion exchange membrane capable of transporting ions of one charge, positive or negative, and having exchangeable ions of the same charge as the matrix ions. The stopped liquid sample is on one side of the membrane. A regenerant liquid stream flows through the regenerant flow compartment on the other side of the membrane from the parked liquid sample. During pretreatment, at least some of the matrix ions in the parked liquid sample flow across the membrane into the regenerant flow compartment to be carried away in the regenerant solution. Thereafter, the liquid sample is removed from the sample compartment. Then, the ionic species in the sample are separated, typically in a chromatography column, and are directed to a detector. This aspect is done using a conventional chromatography system setup.

An important distinction between the pretreatment systems of the present invention and the suppressor pretreatment systems of the prior art is that the liquid sample is parked in the sample compartment of the pretreatment device while suppression is performed. The sample is parked for the desired duration to remove the desired amount of matrix ions from the sample stream to thereby "neutralize" the sample stream of the matrix ions to a sufficient extent so that they do not interfere with analysis. Although the sample stream is stationary during suppression, the regenerant liquid stream flows continuously through the regenerant flow compartment. In this way, the pretreatment device may be continuously regenerated. As discussed above, the suppressors of the prior art may be employed in a continuous or batch mode or intermittent operation. Intermittent operation is illustrated in U.S. Pat. No. 5,569,365.

One suppressor-like pretreatment device which can be used in conjunction with the present invention is sold by Dionex Corporation under the trademark ASRN for a chromatography system for analyzing anions in a base sample stream. Such a pretreatment device, also termed a neutralizer, must be adapted by appropriate valving and a timing electronics or software for use in the parking mode of the present invention in which the liquid sample flows into a sample compartment and is parked there for a predetermined time during suppression.

Parking according to the present invention is capable of suppressing very high concentrations of matrix ions since the neutralizer suppressor is regenerated, preferably continuously, while the sample is neutralized while being stationary. Thus, the only limitation for high concentrations of matrix ions is that substantial time may be required for suppressing or neutralizing a sample. If so, the process of sample neutralization can be performed in parallel with the sample analysis run by the use of appropriate commands in the software to trigger the parking and neutralization of the sample. The volume to be analyzed can be parked into the sample compartment as a sample plug. Alternatively, the sample stream may be suppressed in a stop flow format by continuously moving short segments of the sample stream into the neutralizer device and then neutralizing the sample under no flow or stop flow conditions. In this mode a larger volume of the sample could be suppressed or neutralized as per the present invention.

As set forth above, the pretreatment devices can utilize suppressors of the prior art which are electrolytically or chemically regenerated. For example, the membrane suppressors disclosed in U.S. Pat. No. 4,998,098 are described for either mode of operation. Moreover, the electrolytic suppressor can be used with a regenerant solution which is an acid for cationic matrix ions or a base for anionic matrix ions. As used herein, the term regenerant solution refers to such acidic or basic aqueous solutions as well as solutions which substantially comprise water having no substantial amounts of other compounds. Such substantially water regenerant solutions are preferably used with the electrolytic suppressor devices.

For electrolytic suppressor devices, the current required to suppress a given concentration of matrix ions with 100% faradaic efficiency can be calculated from the equation:

$$I = FCV/60$$

I is the current mA
F is Faraday's constant (coulombs/equiv).
C is the concentration expressed as M
V is the flow rate expressed in ml/min
1 mA=0.62 mM at 1 mL/min The current required to suppress 20 mM of NaOH eluent at a constant flow rate of 1 mL/min (or 0.02 meqv/min) with 100% faradaic efficiency can be calculated as approximately 32 mA. Now in the park and suppress process in order to suppress 20 mM of NaOH in a sample plug of 100 uL (0.002 meqv) at 100% faradaic efficiency one would require 3.2 mA over a one minute duration. Therefore the above equation can be rewritten for the park and suppress concept as $$I_{100\%} = FCv/60t$$

$I_{100\%}$ is the current in mA for a 100% current efficient device
F is Faraday's constant (coulombs/equiv)
C is the concentration (of the suppressed anions or cations)
v is the sample volume in ml
t is the time required in minutes for suppressing the sample By plugging in the time required to suppress a given sample the current required for suppressing the sample can be calculated. In the above equations the assumption was that the process of suppression was 100% current efficient. For suppression devices with lower current efficiency the current requirement increases and can be calculated as $$I_{min} = (I_{100\%} * 100)/(\% \, CE)$$

$I_{min}$ is the minimum current required for a given current efficiency
$I_{100\%}$ is the current required for a 100% current efficient device
% CE is the current efficiency expressed as a %

Therefore, for example, for suppressing a sample comprising 100 uL of a 20 mM NaOH sample, using a suppressor with a current efficiency of 50% for a duration of 1 minute the minimum current required can be calculated as 6.4 mA.

Using the parking method of the present invention, so long as the current exceeds the minimum current value, the sample will be suppressed within the specified duration, (one minute in the previous example). If lower current settings are used, then the sample parking duration needs to be adjusted to a longer time in order to compensate for the lower current. Typically, application of a lower current is only recommended with suppressor devices that have substantial static capacity since the static capacity acts as a reservoir of regenerant ions required for the neutralization reaction. If the static capacity of a given suppressor device is exceeded at a given current (that is lower than the minimum current) then the sample will be partially neutralized. Hence this condition should be avoided.

If the applied current exceeded the minimum current for a given sample, the sample will be suppressed faster. In some suppressor devices it is desirable to apply lower current since the wattage would be lower leading to lower levels of blanks since the leachables from the ion exchange materials are lower at the lower wattage.

It is possible to find the minimum current required for suppressing an unknown sample in the pretreatment device by monitoring the sample after suppression. For example with an NaOH matrix the background after suppression is water. Thus, by monitoring the conductivity of the sample plug for a given applied current one could experimentally derive the minimum current required for suppressing an unknown sample. Typically, currents applied are in the 50 mA to 500 mA regime.

The duration of parking may vary over a wide range depending upon the conditions of suppression and the concentration of the matrix ions. For example, parking for adequate removal of matrix ions to prevent interference can occur in as little as 15 to 60 seconds to 1, 2, 3, 4, 5 or 8 minutes or more.

As set forth above, the present invention can also be implemented with chemical suppressors of the prior art such as the '098 patent. In this case, the chemical regenerant solution (e.g., acid or base) is supplied to the regenerant flow compartment while the sample is parked in the sample compartment. In chemical suppression for a given suppressor device, the concentration and flow rate of the regenerant are primary variables that determines the capacity of the chemical suppressor device. Higher regenerant concentration however can lead to leakage of the regenerant ions which is undesirable. The regenerant concentration as per the present concept can be very low leading to lower regenerant leakage.

Referring to FIG. 1, one embodiment of the invention is illustrated in which the pretreatment device 10 is of the general type sold by Dionex Corporation under the tradename ASRN are as generally illustrated in the sandwich suppressor embodiment of U.S. Pat. No. 4,999,098. It is a flat membrane sandwich suppressor in which ion exchange membranes 12 and 14 define therebetween a sample compartment 16. To the exterior of membranes 12 and 14 are regenerant compartments 18 and 20 through which solutions of regenerant liquid streams 22 and 24, respectively, flow during suppression. For a non-electrolytic membrane suppressor, streams 22 and 24 may be an acid regenerant solution for a cationic matrix ion or base for an anionic matrix ion. As set forth above, the pretreatment device may also be an electrolytic membrane suppressor in which case the regenerant solutions 22 and 24 may be water or a recycled solution as from the detector containing sample analytes or from a post-separation suppressor. Many possibilities exist. Use of effluent recycle from the detector to a post-separation suppressor is illustrated in U.S. Pat. No. 5,352,360.

In the electrolytic sandwich suppressor as illustrated in the prior art, an aqueous liquid stream flows through a hydronium or hydroxide ion source compartment on the opposite side of a second membrane from the sample compartment. The second membrane forms the second wall of the sample compartment.

As set forth above, suppressors other than sandwich membrane suppressors may be employed. Thus, the membranes are of other shapes such as cylindrical or suppressor in which only a single membrane is used separating a single regenerant flow compartment from the sample compartment may be used as illustrated in the '098 patent.

The pretreatment device may include any form of packing or flow-through material, preferably having ion exchange sites of the same charge as the exchangeable ions of the membrane in sample compartment 16 or neutral materials as described in U.S. Pat. No. 6,077,434. Suitable packing includes screens disclosed in the '098 patent and '434 or a flow-through monolith or a packed bed of ion exchange particles such as disclosed in U.S. Pat. No. 5,352,360. In addition, the pretreatment device may be a packed bed suppressor in combination with one or more membranes separating the packed bed from a regenerant liquid stream. A suppressor of this type is illustrated in U.S. Pat. No. 6,495,371.

In the simplified version of FIG. 1, a pump 26 pumps the sample liquid into compartment 16 and the pump is turned off with the solution parked in sample compartment 16. The pump includes a timing controller via standard TTL or relay logic or software interface for turning off the pump for a predetermined duration relative to the desired extent of replacement of the matrix ions in the aqueous sample stream. Thus, for a highly concentrated matrix ion the timing controller is set for a longer duration than a lower concentration of matrix ions. The timing controller may be set by appropriate software which can be adjusted depending on the condition or concentration of the matrix ions. The timing control can be done through TTL or relay switch. Typically, the timing is set to remove the matrix ions to a sufficient extent that they do not substantially interfere with analysis of the ionic species of interest. Alternatively, the timing control can control the timing for parking by switching a valve in communication with the pretreatment device as illustrated in FIG. 4A-E.

In a preferred embodiment, first and second electrodes, not shown, are in electrical communication with the sample compartment and regenerant flow compartment, respectively. In this embodiment a gas removal device may be used to remove the gas from the neutralized sample prior to analysis. In a sandwich suppressor with two membranes, the electrodes typically are on the outside of channels 18 and 20 as illustrated in U.S. Pat. No. 5,352,360 which discloses the electrolytic reactions. For electrolytic suppression, a water containing regenerant flows through channels 18 and 20. The electric field is applied between the electrodes when the sample is parked. In the illustrated embodiment, the sample solution is parked in channel 16 for a sufficient time for the matrix ions to be reduced to a concentration that they do not substantially interfere with analysis. Such reduced concentrations are substantially the same as in a conventional suppressor for suppressing an eluent. During parking, the solution in channels 22 and 24 preferably flows continuously during parking.

Referring again to FIG. 1, when the liquid sample in sample compartment 16 has been parked for a sufficient time for neutralization, the pump is reactivated to pump the solution to a six-way valve 28. The first position of the solution is pumped to sample loop 30 which forms part of a conventional analytical system such as one sold by Dionex Corporation under the trademark ICS2000. In the first valve position, with pump 26 activated, sample solution flows from compartment 16 through valve ports A, F for loading into sample loop 30 and then through ports C and B and diverted to waste. After loading, the valve positions are shifted so that eluent from a source, not shown, is supplied from analytical pump 32 directed to valve 28. In this instance, the solution flows through ports E, F and through sample loop 30 and then through ports C and D and from there to chromatography column 34 through suppressor 36 and from there to a detector 38, suitably a conductivity detector. The portion of the system downstream from the pretreatment device is conventional and is suitably of the type set forth in one or more of the above patents including U.S. Pat. Nos. 5,597,481, 5,325,360 and 4,999,098. If desired, the effluent from detector 38 may be recycled as streams 22 and 24 for pretreatment device 10 after flowing through suppressor 36 as illustrated in U.S. Pat. No. 5,352,360.

Figure 2:
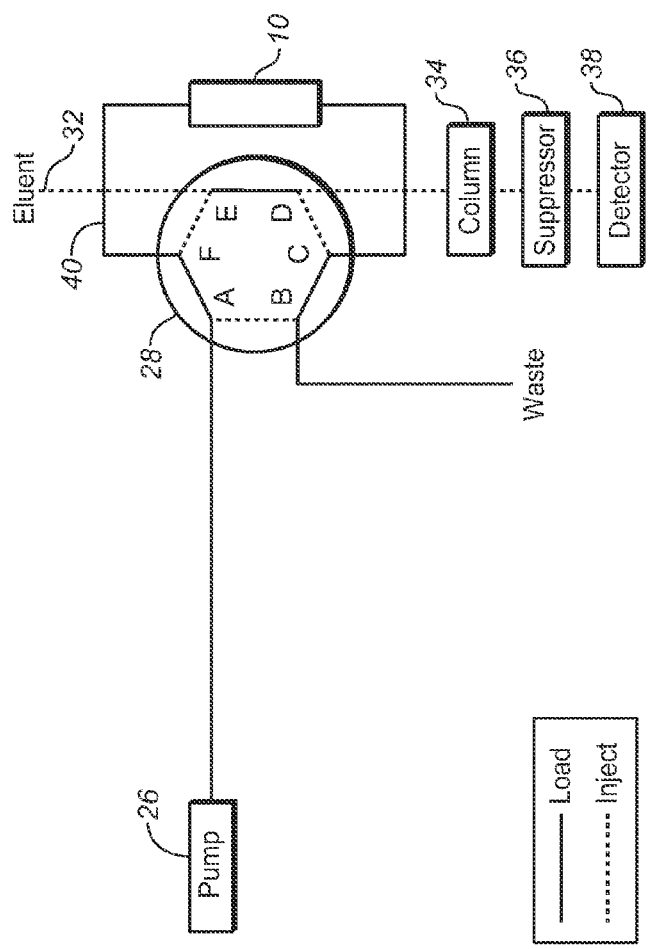

Referring to FIG. 2, in another embodiment, the system of FIG. 1 is illustrated with the exception that the sample injection loop in the conventional system is replaced by a suppressor-like device of the type described above. Thus, suppression of the sample in a pretreatment device-like device 10 can take place in the sample compartment 16 of pretreatment device 10 illustrated in FIG. 1 which also serves as the sample loop. Like parts are designated with like numbers in FIGS. 1 and 2. The combined sample injection loops/pretreatment device is designated by the number 40 and defines the total injection volume. In this embodiment the neutralizer device preferably is a high pressure compatible device since this device is on the high pressure side of the separator column.

Figure 3:
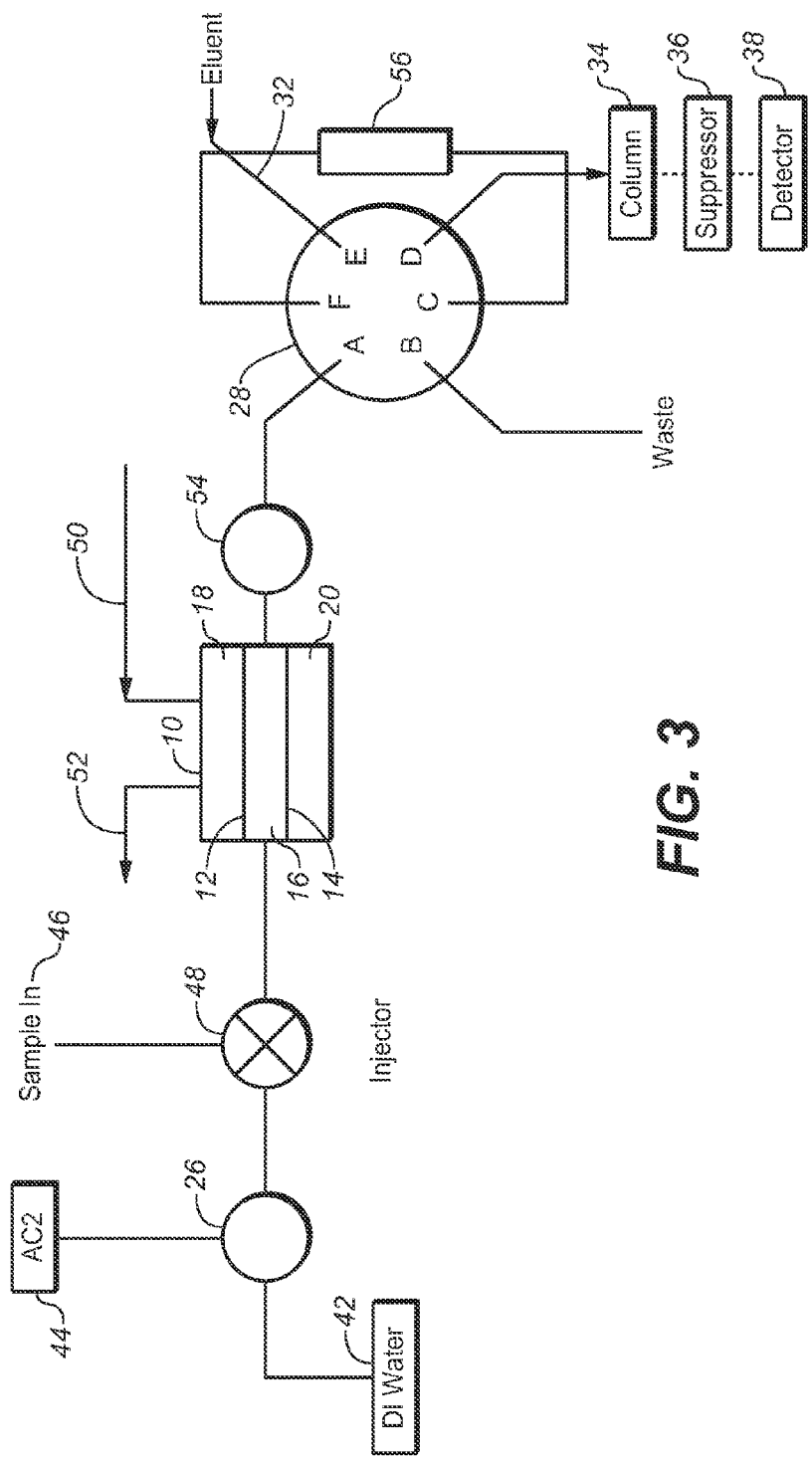

In another embodiment illustrated in FIG. 3, an ionic species concentration column is disposed downstream of and in fluid communication with the pretreatment device for collecting and concentrating the ionic species. The ionic species concentration column is in fluid communication with the inlet of a separator, preferably a chromatography column. The portion of this system may be of the type of system as illustrated in U.S. Pat. No. 5,597,481 or as sold by Dionex Corporation under the trademark ICS2500.

A suitable complete system of this type is illustrated in FIG. 3. Like parts in FIGS. 1 and 3 are designated with like numbers. A sample displacing stream 42 (DI water in this embodiment) is pumped by pump 26 into a standard injection valve 48. An AC2 controller 44 from Dionex is used to turn off the pump 26 through TTL control. The sample 46 is loaded into a sample injection loop (details not shown) in valve 48 and then is loaded into the sample compartment 16 of the pretreatment neutralizer device 10 by the pump flow from pump 26. The sample is parked in the sample compartment 16 by stopping the flow from pump 26 at a set time through a TTL command control of the AC2 controller 44. The sample is neutralized in the sample channel compartment 16 as described above regarding FIG. 1. After a period of time the neutralized sample is diverted into a conductivity cell 54 by turning ON the pump 26 via TTL command control of the AC2 controller 44. The neutralized sample conductivity is monitored via conductivity cell 54 and then the sample is diverted into a valve 28, which is a standard injection valve of a conventional chromatography system. The sample stream displaced by the sample displacing stream is loaded into a preconcentrator column 56 by routing the sample from port A to F and then through the concentrator column into port C and B and then diverted to waste liquid (e.g. water or eluent) to displace the aqueous liquid sample and transport it to and from the neutralizer pretreatment device. This is the load position. The sample ions are concentrated in the concentrator column 56. In the inject position the sample displacing stream is routed from port A to port B and then to waste. The eluent stream 32 from a conventional chromatography system is plumbed to valve 28.

In the load position the eluent stream 32 is routed from port E to port D and then to the column 34 and into a suppressor 36 and then through a conductivity detector cell 38 for detecting the analytes. In the inject position the eluent line 32 is connected via port E to port F and then the eluent elutes the retained ions on the concentrator column 56 and then enters port C. The eluent is then routed via port D to the Column 34 and so on.

Another preferred embodiment of the present invention is shown in FIGS. 4A through E. The FIGS. 4A though E differ in valve positions. In this embodiment the sample displacing stream flow carries the sample plug and by diverting this stream using a valve the sample parking step is achieved according to the present invention.

Figure 4A:
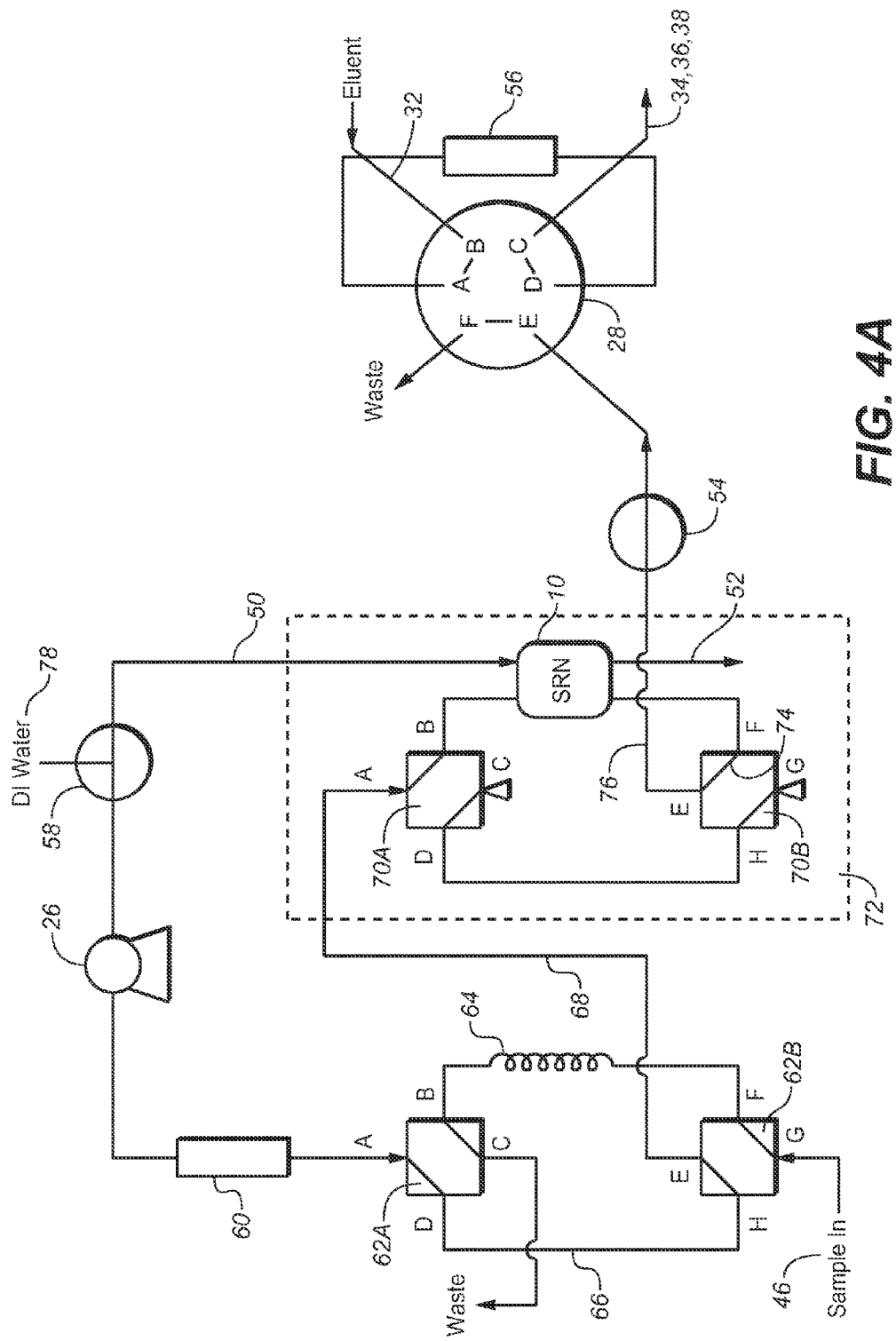

Referring to FIG. 4A the valve position facilitates the loading of the sample stream into the sample injection loop 64. The rest of the plumbing facilitates pumping the sample displacing stream into injection valve 28 of a conventional chromatography system.

Specifically, the sample is pumped into valve 62B at port G and is routed through port F into a sample loop 64. The sample stream is then diverted to port B of valve 62A and then is routed to waste via port C.

The sample displacing stream (DI water) 78 is split using a standard tee junction 58 and then the first split stream is pumped using the pump 26 into a guard polishing column 60 that purifies the water from ionic impurities. This stream is designated the displacing stream and is then routed through a valve 62A at port A and then through port D and conduit 66 through valve 62B via port H and E and through conduit 68 into valve 70A. Further the displacing stream is diverted through port A and B into the sample compartment (not shown) of a SRN pretreatment neutralizer device. The stream is then routed out and diverted via valve 70B from ports F and E to a conductivity cell 54 which is then routed to an injection valve 28 of a conventional chromatography system via port E and F and then diverted to waste. The splitter 58 allows a second stream of the DI water from the reservoir (not shown) to be diverted into the regenerant channels of the SRN neutralizer device via conduit 50. This stream carries away the matrix ions to waste via conduit 52.

Figure 4B:
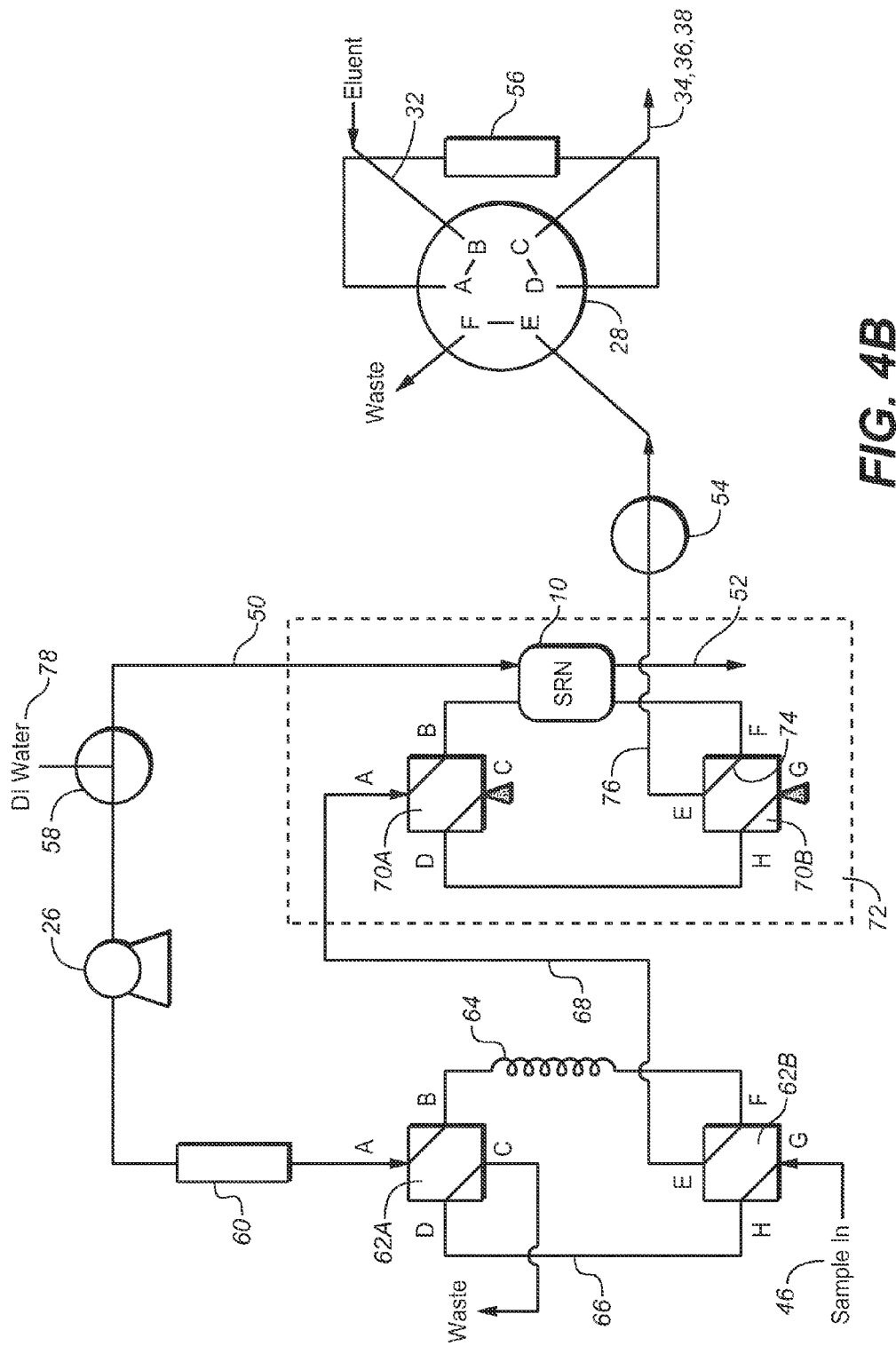

Referring to FIG. 4B the valve position facilitates the injection of the sample plug from the sample loop 64 by displacing the sample plug with the displacing liquid. Further the valve position on the dual stack valve 70A and B allowed the sample slug to be parked within the sample compartment (not shown) of a SRN pretreatment neutralizer device 10.

Specifically, the sample displacing stream (DI water) 78 is split using a standard tee junction 58 and then the first split stream is pumped using the pump 26 into a guard polishing column 60 that purifies the water from ionic impurities. The displacing stream is then routed through a valve 62A at port A and then is routed through port B and displaces the sample slug from sample loop 64 in a direction that is opposite to the sample load direction and diverts the sample slug into conduit 68 via ports F and E on the valve 62B. From conduit 68 the sample slug is diverted into port A of valve 70A and then routed into the sample compartment (not shown) of an SRN pretreatment neutralizer device 10. Valve 62A and B are arranged in an orientation that allows the sample stream to be connected via ports G, H, conduit 66, D and C to waste. The rest of the flow stream routing is similar to what was described earlier for FIG. 4A.

Figure 4C:
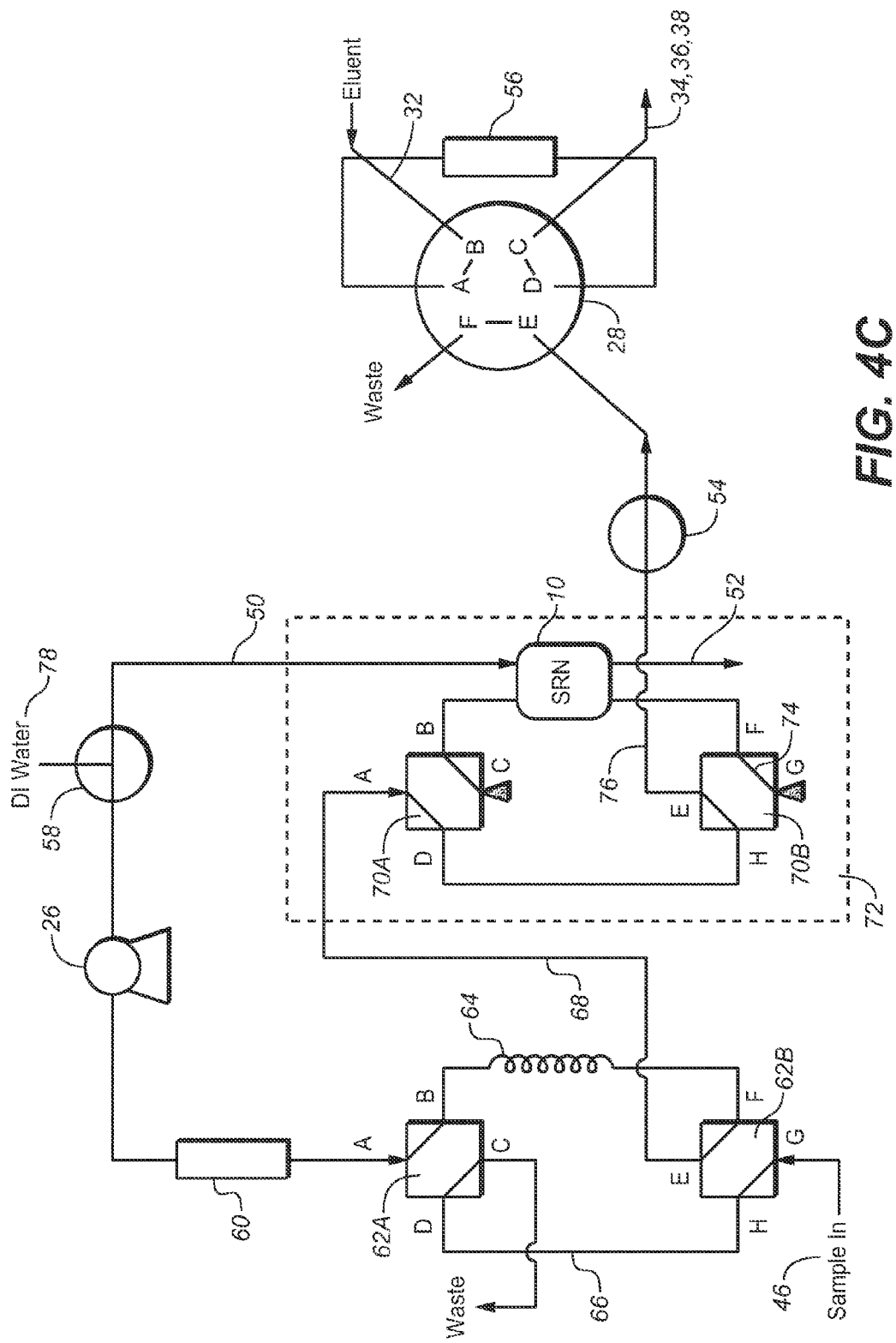

After a predetermined time (that can be optimized based on the delay volume from the sample injection loop to the sample compartment of an SRN pretreatment neutralizer device) the sample is loaded on to the sample compartment as described in previous paragraph and then valve 70A and B are switched to divert the displacing liquid stream away from the SRN neutralizer. This is accomplished as per the present invention and is shown in FIG. 4C by routing the stream from conduit 68 into valve 70A port A to port D and then to valve 70B port H to Port E and so on. Note under these conditions there is no fluidic movement in the line from valve 70A port C to B through the sample compartment of the SRN neutralizer 10 through line 74 into port F and G on valve 70B. The ports C and G have plugs and prevents flow out of these ports. In the above orientation the sample is parked and undergoes neutralization according to the present invention.

Figure 4D:
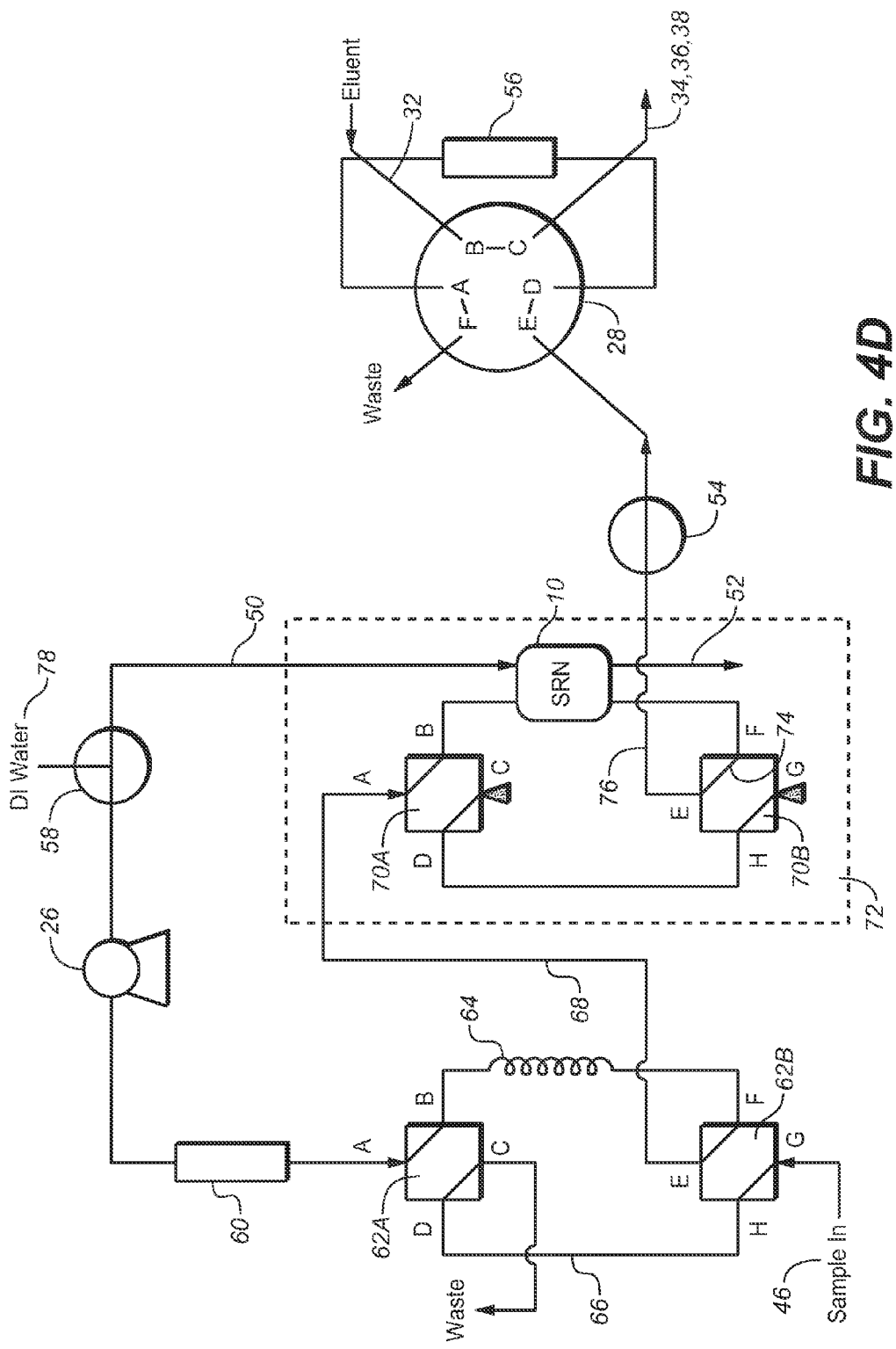

After a predetermined time based on the matrix ion concentration, volume of the sample and applied current, the valve configuration in 70A and B is switched to facilitate flow of the sample plug. This is shown in FIG. 4D. In this orientation the stream is diverted back into the sample compartment of the neutralizer and the specific movement of the liquid stream is identical to what was described in FIG. 4B with the exception that the neutralized sample is now routed to valve 28 which is now in the sample load position. Specifically the neutralized sample is routed via conduit 74 into port F and E on valve 70B and then routed via conduit 76 into the conductivity cell 54. The conductivity of the sample can be monitored to ensure that the sample is neutralized to the desired extent and then the sample stream is routed via port E and D on valve 28 into the concentrator column 56. The sample ions are concentrated in the concentrator column and the unretained components are diverted via port A and F on valve 28 to waste.

Figure 4E:
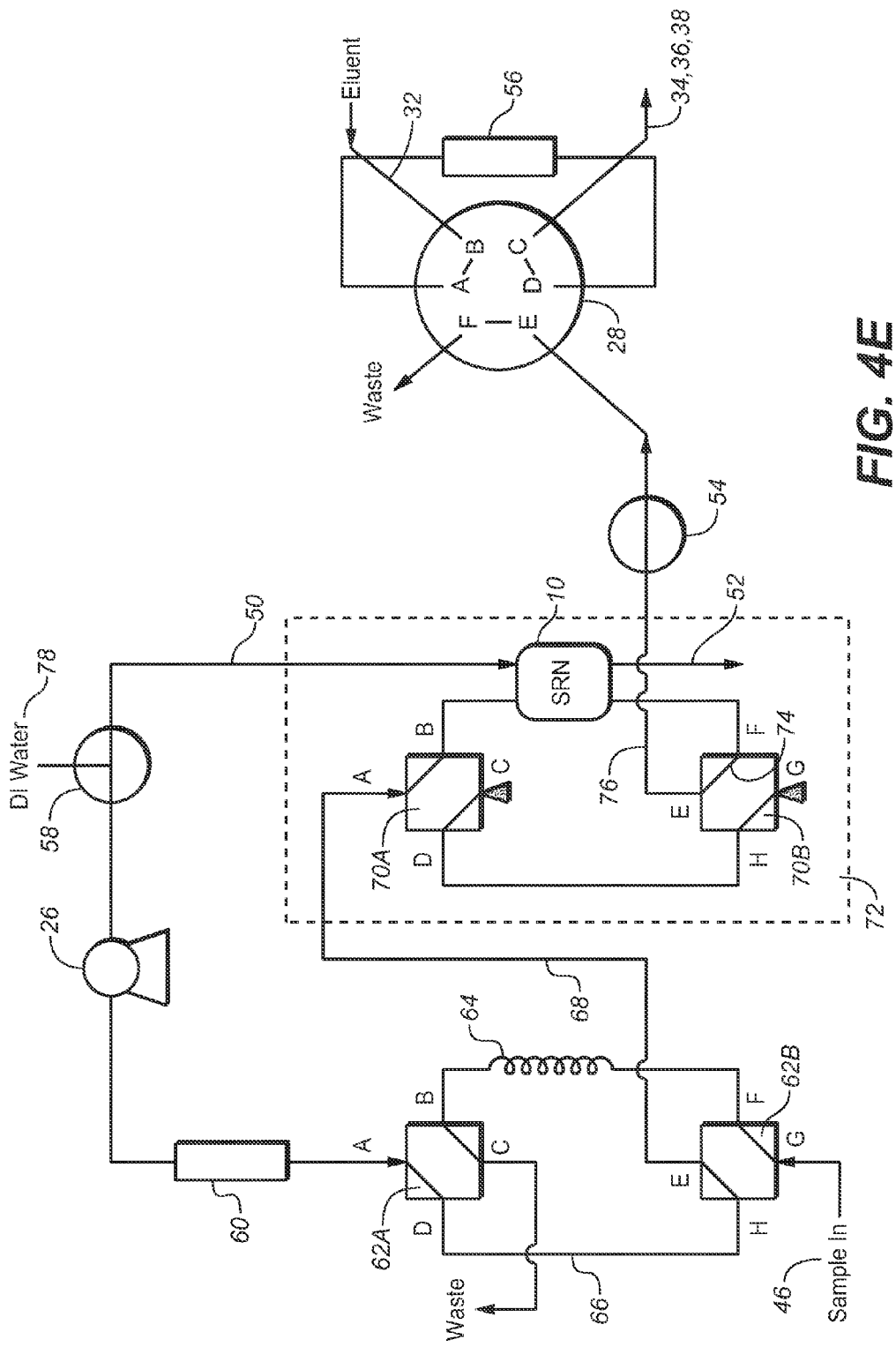

FIG. 4E illustrates the injection of the neutralized sample for analysis in a conventional chromatography system. In this configuration the Eluent stream 32 is routed through the port B and A on valve 28 and elutes the ions retained on the concentrator column 56. The eluted ions are routed via port D and C on valve 28 into the separator column 34, suppressor 36 and detector 38. In non suppressed applications the suppressor 36 can be eliminated in the above configuration. The valve 62A and B under these conditions are ready for sample loading as outlined for FIG. 4A.

In the above embodiment the displacing stream is used to load the sample into the neutralizer and by diverting this stream parking is accomplished. The neutralized sample is displaced out of the neutralizer and is routed into a concentrator column for further analysis. It should be noted that during the analysis the steps of 4A through D could be accomplished thereby saving the cycle time for sample neutralization.

In order to illustrate the present invention, the following non-limiting examples are provided.

EXAMPLES

Example 1

FIG. 3 shows the experimental setup for implementing a preferred embodiment of the present invention. A pump was used to park the sample into the suppressor/neutralizer device that was operated in the external water mode of operation. The pump was turned off using an AC2 control module from Dionex. The timing was adjusted to ensure that the injected sample was parked in the eluent channel of the suppressor or neutralizer device. After suppression the sample was routed to a concentrator column located on an injection valve that was installed in a standard ion chromatography system. Analysis of the sample was done in a standard manner.

Example 2

This example shows the analysis of trace anions in 50% base solution from Fisher Scientific. A DX600 ion chromatograph from Dionex was used in this work. A DXP pump was operated at 0.3 ml/min and pumped DI water into the sample injection valve and was used to park a 25 uL sample volume in the eluent channel of an ASRS Ultra II suppressor unit from Dionex. The dead volume from the connecting tubing from the injection valve to the suppressor eluent in port was estimated, and based on the flow rate the pump was timed and turned off, ensuring that the sample was parked in the eluent channel of the ASRS Ultra II suppressor. The ASRS Ultra II suppressor was operated at 300 mA and in the external water mode of operation. The sample was parked for 4 minutes in the suppressor to neutralize the base. The sample was then diverted into a 4×35 mm TACLP1 concentrator column from Dionex by turning on the DI water pump. Analysis of the concentrated anions was done using a 2 mm AS15 column with 38 mM KOH at 0.3 ml/min. The suppressor in the analysis system was a 2 mm ASRS Ultra II suppressor that was operated at 50 mA in the recycle mode of operation. FIG. 4 shows the chromatogram obtained from the above analysis and showed the presence of Flouride (1), Acetate (2), Formate (3), Chloride (4), Carbonate (5), Sulfate (6) and Oxalate (7) in the 50% base sample. The chromatogram also includes the 4 minute neutralization step. Chloride (4) was the biggest contaminant. Note the above analysis was not possible without the neutralization step. The above demonstrates the utility of the present invention for neutralizing a base matrix.

Example 3

Figure 5:
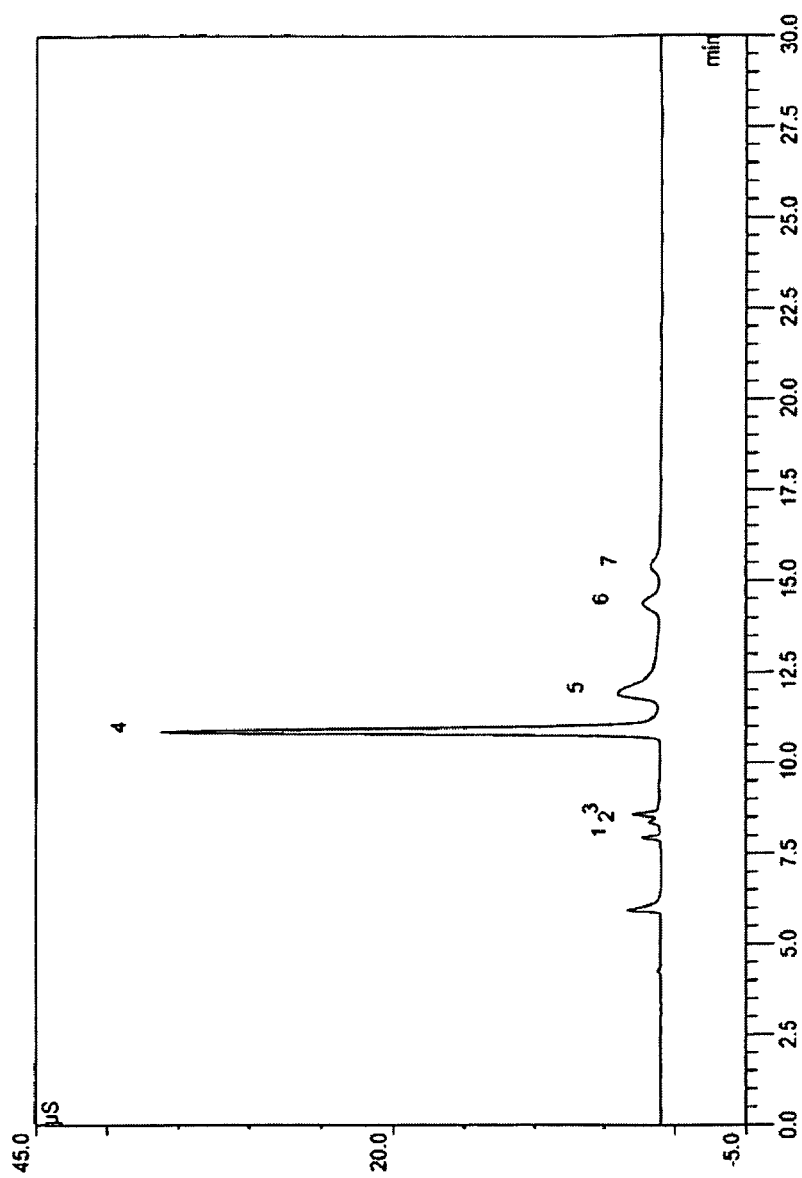
FIG. 5-9 are chromatograms of systems using the pretreatment method of the present invention.
Figure 6:
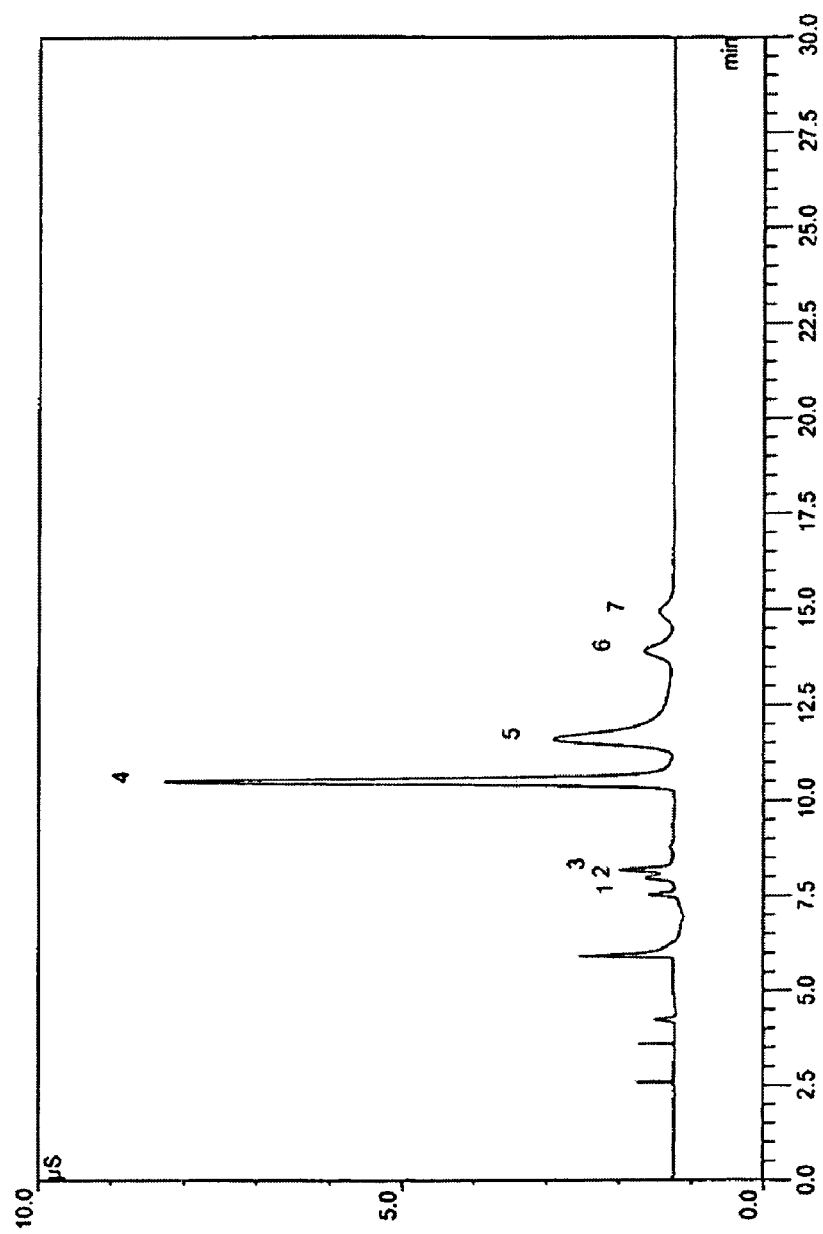

All experimental conditions were identical to example 2 except the sample used was 45% KOH from Fisher Scientific. The above sample contained similar ionic contaminants as example 1 and is shown in FIG. 5. Chloride (4) was the biggest contaminant in this sample. A system blank is shown in FIG. 6 comprising a DI water injection and shows carbonate (5) to be the major peak with acetate (2) as a minor peak. Due to the ability to apply low currents for the neutralization step, the method of the present invention results in minimal blank levels and is suited for the above analysis.

Example 4

Figure 7:
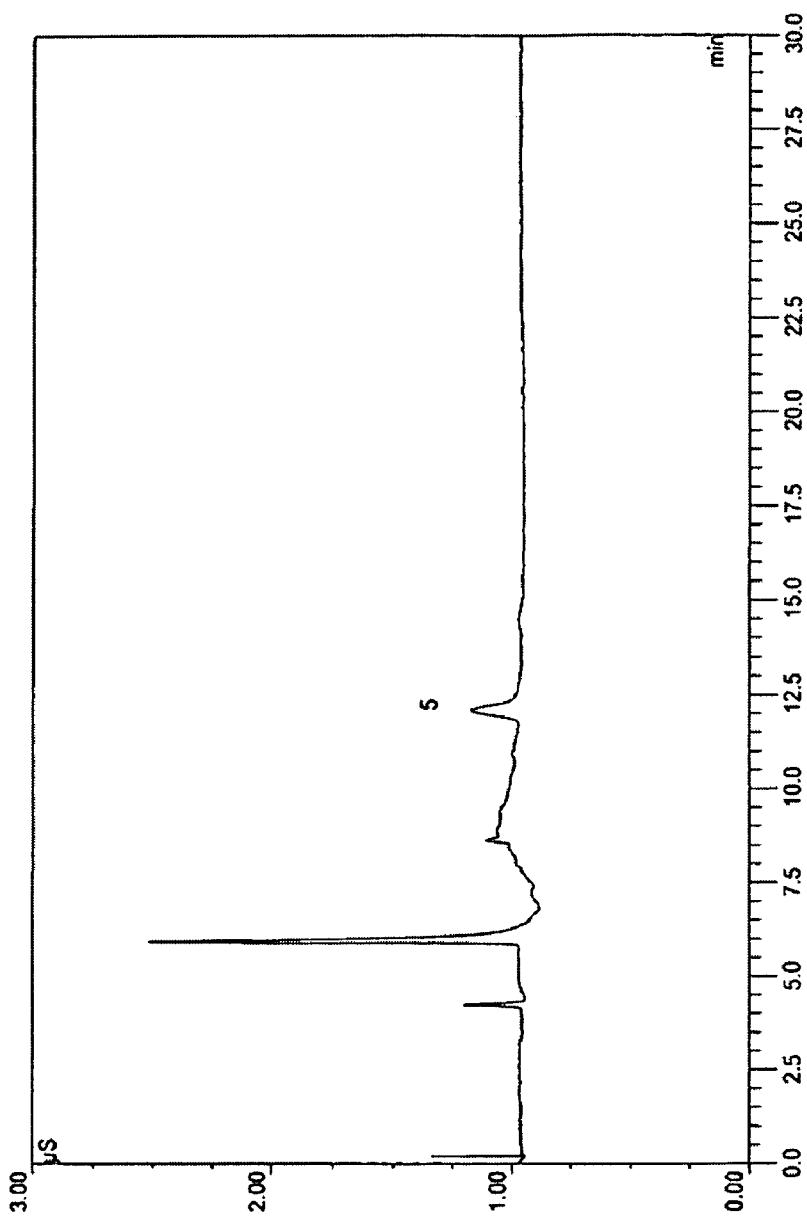

This example shows the analysis of trace cations in 50% methanesulfonic acid from Fluka. A DX600 ion chromatograph from Dionex was used in this work. A DXP pump was operated at 0.5 ml/min and pumped DI water into the sample injection valve and was used to park a 100 uL sample volume in the eluent channel of a CSRN Neutralizer unit from Dionex. The dead volume from the connecting tubing from the injection valve to the suppressor eluent in port was estimated and based on the flow rate the pump was timed and turned off ensuring that the sample was parked in the eluent channel of the CSRN. The CSRN was operated at 300 mA and in the external water mode of operation. The sample was parked for 8 minutes in the neutralizer in order to neutralize the acid. The sample was then diverted into a 4×35 mm TCCLP1 concentrator column from Dionex by turning on the Di water pump. Analysis of the concentrated cation analytes was done using a 4 mm CS12A column with 20 mM MSA eluent at 1.0 ml/min. The suppressor in the analysis system was a CSRS Ultra II suppressor that was operated at 59 mA current in the recycle mode of operation. FIG. 7 shows the chromatogram obtained from the above analysis and showed the presence of sodium (3), ammonium (4), potassium (6), magnesium (8) and calcium (9). Sodium and the divalent cations were the major contaminants in this acid sample. Several unidentified peaks were found in the chromatogram. Note the above analysis was not possible without the neutralization step. The above demonstrates the utility of the present invention for neutralizing a acid matrix.

Example 5

Figure 8:
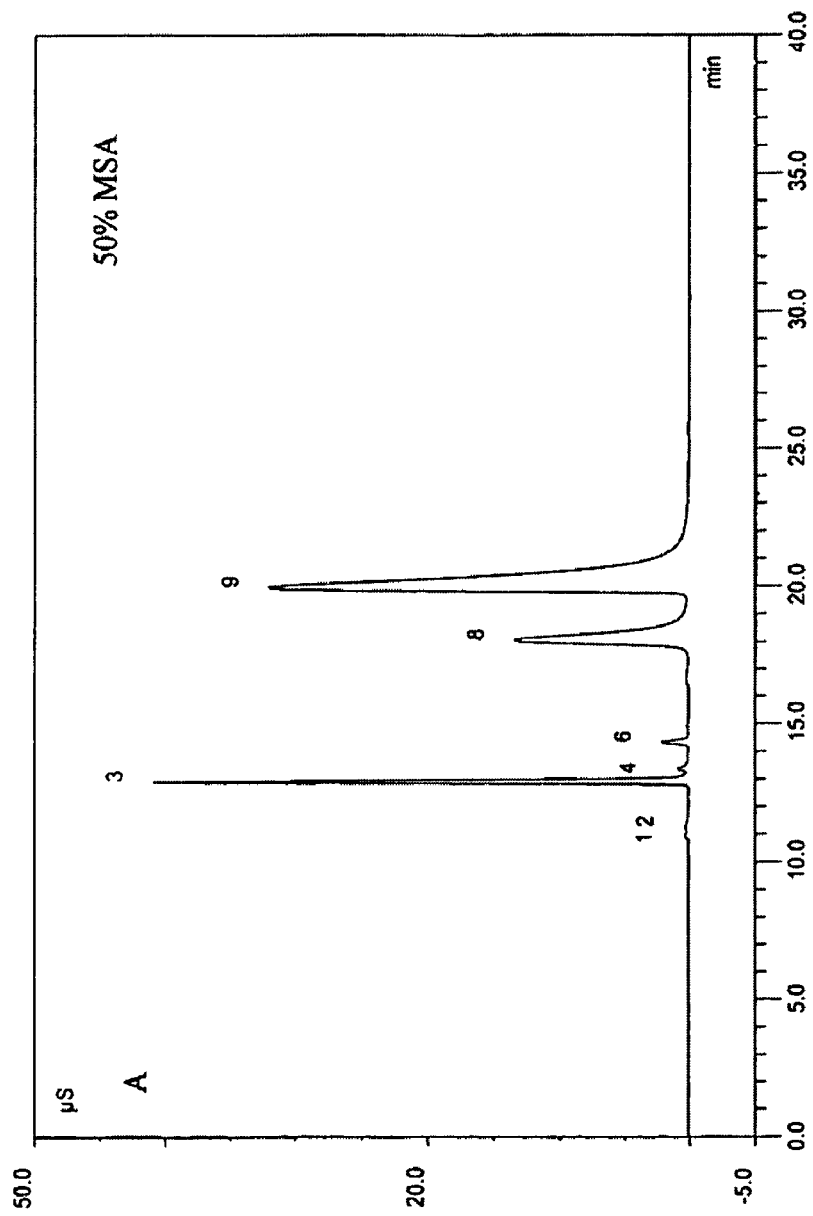
Figure 9:
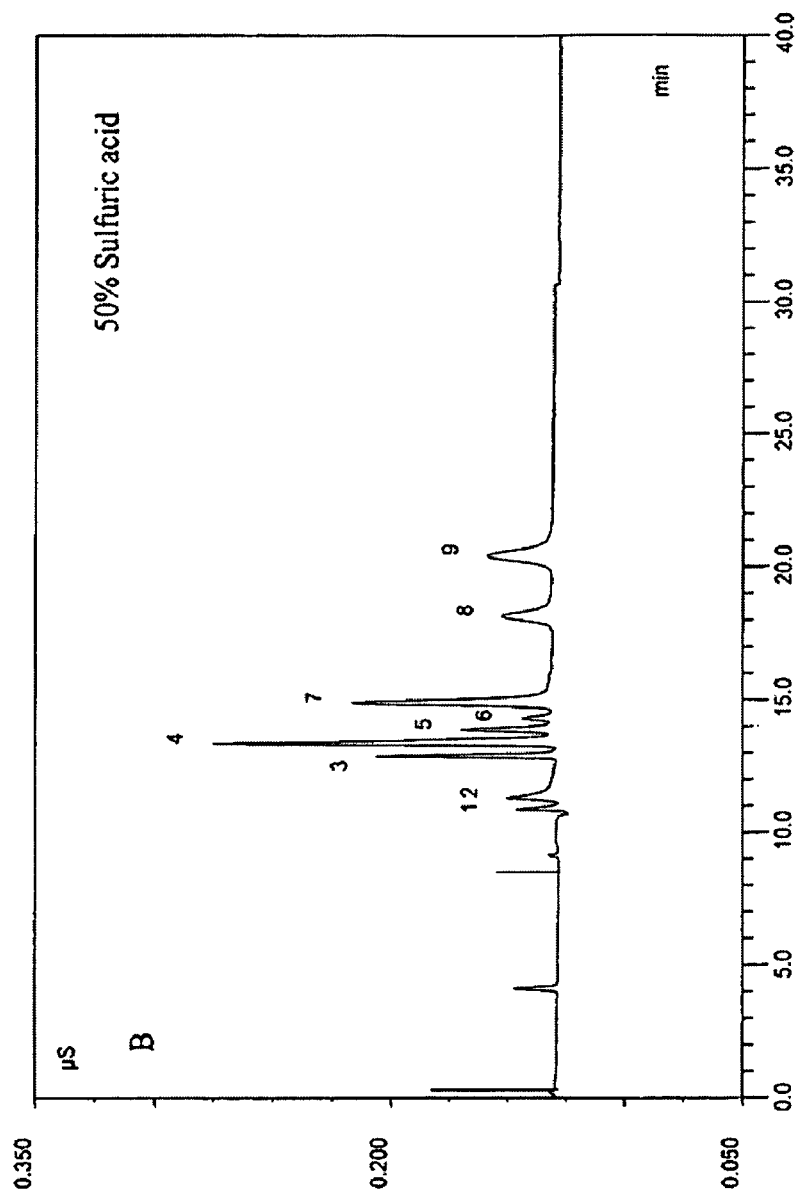

All experimental conditions were identical to example 4 except the sample used was 50% sulfuric acid from JT Baker Company. The above sample also contained similar ionic contaminants as example 4 but in varying amounts and is shown in FIG. 8.

What is claimed is:

1. An analytical apparatus for analyzing ionic species comprising
   (a) a pretreatment device for pretreating an aqueous sample stream comprising a plurality of ionic species to be detected and at least one matrix compound for removing at least part of the matrix ions of such matrix compound, said matrix ions being of opposite charge to said ionic species, and replacing said matrix ions with hydroxide or hydronium ions, said pretreatment device including
      (1) a sample compartment having an inlet and an outlet,
      (2) a regenerant compartment having an inlet and an outlet,
      (3) at least one ion-exchange membrane partitioning said sample compartment and said regenerant compartment, said one ion-exchange membrane being preferentially permeable to ions of one charge only, positive or negative, of the same charge as said matrix ions, and including exchangeable ions of said one charge, (b) a separator comprising chromatographic medium for separating the ionic species in said pretreated sample stream in fluid communication with said sample compartment outlet, and (c) a detector for detecting said separated ionic species in fluid communication with said separator, (d) a pump for transporting aqueous sample through said pretreatment device, and (e) a timing controller for turning off said pump or switching a valve in communication with said pretreatment device for a predetermined duration related to the desired extent of replacement of said matrix ions in said aqueous sample.

2. The apparatus of claim 1 further comprising first and second electrodes in electrical communication with said sample compartment and said regenerant flow compartment, respectively.

3. The apparatus of claim 1 further comprising an ionic species concentration column disposed downstream of and in fluid communication with said pretreatment device for collecting and concentrating said ionic species, said ionic species concentration column also being in fluid communication with said separator.

4. The apparatus of claim 1 in which the sample compartment of said pretreatment device comprises a sample injection loop for injection of sample into said apparatus to be pumped to said separator.

* * * * *